US010354224B2

(12) United States Patent
Tohma (10) Patent No.: US 10,354,224 B2
(45) Date of Patent: Jul. 16, 2019

(54) CLINICAL LABORATORY SYSTEMS, METHODS AND COMPUTER PROGRAMS FOR MANAGING CLINICAL LABORATORY WORK, MANAGEMENT DEVICES, AND TERMINAL DEVICES

(75) Inventor: Ryuichi Tohma, Akashi (JP)

(73) Assignee: SYSMEX CORPORATION, Hyogo (JP)

( * ) Notice: Subject to any disclaimer, the term of this patent is extended or adjusted under 35 U.S.C. 154(b) by 2430 days.

(21) Appl. No.: 10/703,935

(22) Filed: Nov. 7, 2003

(65) Prior Publication Data

US 2005/0102166 A1    May 12, 2005

(51) Int. Cl.
| | |
|---|---|
| G06Q 10/00 | (2012.01) |
| G06Q 50/00 | (2012.01) |
| G06Q 10/10 | (2012.01) |
| G06Q 50/24 | (2012.01) |

(52) U.S. Cl.
CPC ............. *G06Q 10/10* (2013.01); *G06Q 50/24* (2013.01)

(58) Field of Classification Search
CPC ............................... G06Q 10/10; G06Q 50/24
USPC ...................... 705/2–4; 364/413.01
See application file for complete search history.

(56) References Cited

U.S. PATENT DOCUMENTS

| | | | |
|---|---|---|---|
| 5,077,666 A | | 12/1991 | Brimm et al. |
| 5,171,977 A | * | 12/1992 | Morrison ............... A61B 5/117 235/375 |
| 5,265,010 A | * | 11/1993 | Evans-Paganelli et al. ................. 600/301 |
| 5,740,800 A | * | 4/1998 | Hendrickson et al. ........ 600/300 |
| 6,018,713 A | * | 1/2000 | Coli et al. .......................... 705/2 |
| 7,089,235 B2 | * | 8/2006 | Dettinger et al. |
| 7,127,310 B1 | * | 10/2006 | Barto ............... G05B 19/41865 700/100 |
| 2003/0065669 A1 | * | 4/2003 | Kahn et al. ................... 707/100 |

(Continued)

FOREIGN PATENT DOCUMENTS

| | | |
|---|---|---|
| JP | 60-225252 A | 11/1985 |
| JP | 11-51942 | 2/1999 |
| JP | 2001-142895 A | 5/2001 |

OTHER PUBLICATIONS

Georgakopoulos et al. "An Overview of Workflow Management: From Process Modeling to Workflow Automation Infrastructure" http://www.workflowpatterns.com/documentation/documents/workflow95.pdf.*

(Continued)

*Primary Examiner* — Hiep V Nguyen
*Assistant Examiner* — Trang T Nguyen
(74) *Attorney, Agent, or Firm* — Brinks Gilson & Lione (57) ABSTRACT

A clinical laboratory system for managing clinical laboratory work is described that includes: an examination information input means for inputting examination information relating to clinical laboratory work; an examination information memory means for storing input examination information; an extraction means for extracting examination information meeting a predetermined extraction condition related to progress of an examination from among stored examination information; a screen preparation means for creating a progress management screen for displaying extracted examination information; and an output means for outputting the progress management screen. Methods and computer programs for managing clinical laboratory work, management devices, and terminal devices are also described.

30 Claims, 9 Drawing Sheets

(56) References Cited

U.S. PATENT DOCUMENTS

2003/0120633 A1\* 6/2003 Torre-Bueno .......... G16H 10/40
2004/0002932 A1\* 1/2004 Horvitz ................ G06N 99/005
706/46

OTHER PUBLICATIONS

Georgakopoulos et al. "An Overview of Workflow Management: From Process Modeling to Workflow Automation Infrastructure p. 119-153"http://www.workflowpatterns.com/documentation/documents/workflow95.pdf (Year: 1995).\*

\* cited by examiner

Fig.1

Individual records

| Reception No. | Patient name | Patient ID | Rush | Assay item | Sample/Analyzer code |
|---|---|---|---|---|---|
| 110001 | Toa Taro | TT0019 | — | WBC·RBC | H1 |
| 110002 | Toa Taro | TT0019 | — | Urinary RBC | U2 |
| 110009 | Toa Jiro | TJ0002 | — | RET | H2 |
| 211001 | Toa Jiro | TJ0002 | — | Urinary protein | U1 |
| 211004 | Toa Hana | TH0001 | Rush | WBC | H1 |
| ... | . . | . . | . | . | . |

*Fig.2*

Individual records

| Reception No. | Pat name | eption time | Arrival (in lab) | Assay | Assay result | Validation | Re-exam ination | Report | . |
|---|---|---|---|---|---|---|---|---|---|
| 110001 | Toa | 10:00 | ○ 10:25 | ○ 10:40 | WBC4000/ | ○ 10:55 | — | ○ 11:00 | . |
| 110002 | Toa | 10:05 | ○ 10:30 | ○ 10:35 | CAST////// | ○ 11:00 | — | — | . |
| 110009 | Toa | 10:15 | ○ 10:35 | ○ 10:45 | RBC/////** | — | 11:00 | — | . |
| 211001 | Toa | . | . | . | . . . | . | . | . | . |
| 211004 | Toa H | . | . | . | . . . | . | . | . | . |
| . . | . . | . | . | . | . . . | . | . | . | . |

"Analyzer ME-1" extraction criteria

| (1) | Analyzer ME-1 is used for the assay. |
|---|---|
| (2) | Validation is not completed within 45 minutes (10 minutes for rush examinations) after sample arrival. |
| (3) | Re-examination instructions are issued. |
| (4) | Re-examination completed for samples for which re-examination instruction have been issued. |
| Combination form: (1)×((2)+(3)+(4)) | |

*Fig. 7a*

"All" extraction criteria

| (5) | Sample arrival not confirmed within 15 minutes (5 minutes for rush examinations) after reception. |
|---|---|
| (6) | Assay not completed within 40 minutes (10 minutes for rush examinations) after sample arrival. |
| (7) | FAX Report not sent within 50 minutes (15 minutes for rush examinations) after sample arrival. |
| Combination form: (5)+(6)+(7) | |

CLINICAL LABORATORY SYSTEMS, METHODS AND COMPUTER PROGRAMS FOR MANAGING CLINICAL LABORATORY WORK, MANAGEMENT DEVICES, AND TERMINAL DEVICES

BACKGROUND

The present invention relates to clinical laboratory systems connecting computers and analyzers through a network for managing examination information relating to clinical examinations. The present invention provides clinical laboratory systems for use particularly in medical treatment facilities, such as in hospitals and the like, for facilitating the managed progress of various types of clinical laboratory work.

In medical treatment facilities such as hospitals and the like, clinical laboratory systems have become widely used for the general management of various types of clinical examination work. Such clinical laboratory systems are constructed by installing analyzers and computers (clients) as input/output terminal devices at various locations in the hospital, and connecting these with a management device such as a computer (server) over a network. Clinical examination work includes examination scheduling and reception, printing barcode labels to adhere to specimen containers, such as blood vials and the like, printing worksheets for examination sequence guidelines, transporting specimens to the laboratory, assaying specimens used in various types of analyzers, tabulating assay results, validation (validation of assay results), re-examination instruction, information on examination results, and the like.

In clinical laboratory work, examination and treatment of the patient may be hindered if examination results are not reported within a fixed time. This kind of problem may arise from various factors including: a specimen collected from a patient not arriving at the laboratory provided with the analyzer within a scheduled time for various reasons; examinations in the laboratory may be fully scheduled; and the transmission of the post-assay report may be incomplete. If problems with a specific specimen are not attended to in a timely manner, not only is the handling of that particular specimen impaired, but the smooth flow of the chain of laboratory work is also hindered. Clinical laboratory systems provided with a progress management function for discovering such problems are known. Such clinical laboratory systems are provided with a function for displaying a list of the progress of each examination which is a management object of the clinical laboratory system. Operators of the clinical laboratory system look for problems in the progress of examinations on a list display, and implement solutions to eliminate any problems found.

In conventional clinical laboratory systems, however, the number of examinations to be monitored in the progress flow increases in conjunction with increases in the number of specimens and types of examinations which are managed by the clinical laboratory system. There are times when there are no problems or few problems in the examinations listed on the display. In other instances, even if there is a problem, the problem examination may be outside the scope of examinations for which the operator is authorized. Consequently, it may be difficult to quickly discover problems with the progress of examinations within the management scope of the operator when many examinations are listed on a display, and this situation prevents rapid resolution of such examination problems.

SUMMARY

The scope of the present invention is defined solely by the appended claims, and is not affected to any degree by the statements within this summary.

A first clinical laboratory system for managing clinical laboratory work embodying features of the present invention includes: an examination information input means for inputting examination information relating to clinical laboratory work; an examination information memory means for storing input examination information; an extraction means for extracting examination information meeting a predetermined extraction condition related to progress of an examination from among stored examination information; a screen preparation means for creating a progress management screen for displaying extracted examination information; and an output means for outputting the progress management screen.

A second clinical laboratory system for managing clinical laboratory work embodying features of the present invention includes a management device and first and second terminal devices connected to the management device with a network. The first terminal device transmits examination information relating to clinical laboratory work input by an input means of the first terminal device to the management device via the network. The management device receives and stores the examination information, extracts examination information meeting a predetermined extraction condition related to progress of an examination from stored examination information, and transmits the examination information thus extracted to the second terminal device via the network. The second terminal device receives the examination information thus transmitted, and outputs a progress management screen displaying the examination information to an output means of the second terminal device.

A method for managing clinical laboratory work includes: inputting examination information relating to clinical laboratory work; storing input examination information; extracting examination information meeting a predetermined extraction condition related to progress of an examination from among stored examination information; creating a progress management screen for displaying extracted examination information; and outputting the progress management screen.

A computer program for managing clinical laboratory work embodying features of the present invention may be included on a storage medium and includes: a function for receiving input examination information relating to clinical laboratory work from an input means, and for storing the examination information in a memory means; a function for extracting examination information meeting a predetermined extraction condition related to progress of an examination from among stored examination information; a function for creating a progress management screen for displaying extracted examination information; and a function for outputting the progress management screen.

A management device for managing clinical laboratory work embodying features of the present invention is connected to first and second terminal devices with a network and includes: a memory means for storing examination information relating to clinical laboratory work input by the first terminal device via the network; an extracting means for extracting examination information meeting a predetermined extraction condition related to progress of an examination from among stored examination information; and a transmitting means for transmitting the examination information thus extracted to the second terminal device via the network. The management device makes the second terminal device display a progress management screen for displaying the examination information thus extracted.

A first terminal device for managing clinical laboratory work embodying features of the present invention is connected to a management device with a network and includes: an examination information inputting means for inputting examination information relating to clinical laboratory work; a transmitting means for transmitting the examination information to the management device via the network; a receiving means for receiving desired examination information meeting a predetermined extraction condition related to progress of an examination; and an output means for outputting a progress management screen displaying the desired examination information.

A second terminal device for managing clinical laboratory work embodying features of the present invention is connected to a management device with a network and includes: a first screen output means for outputting a group selecting screen for selecting a group of examination information relating to clinical laboratory work; and a second screen output means for outputting a progress management screen for displaying desired examination information in the group thus selected.

DETAILED DESCRIPTION

Embodiments of a clinical laboratory system embodying features of the present invention are described hereinafter. However, the present invention is not limited to these embodiments.

Figure 1:
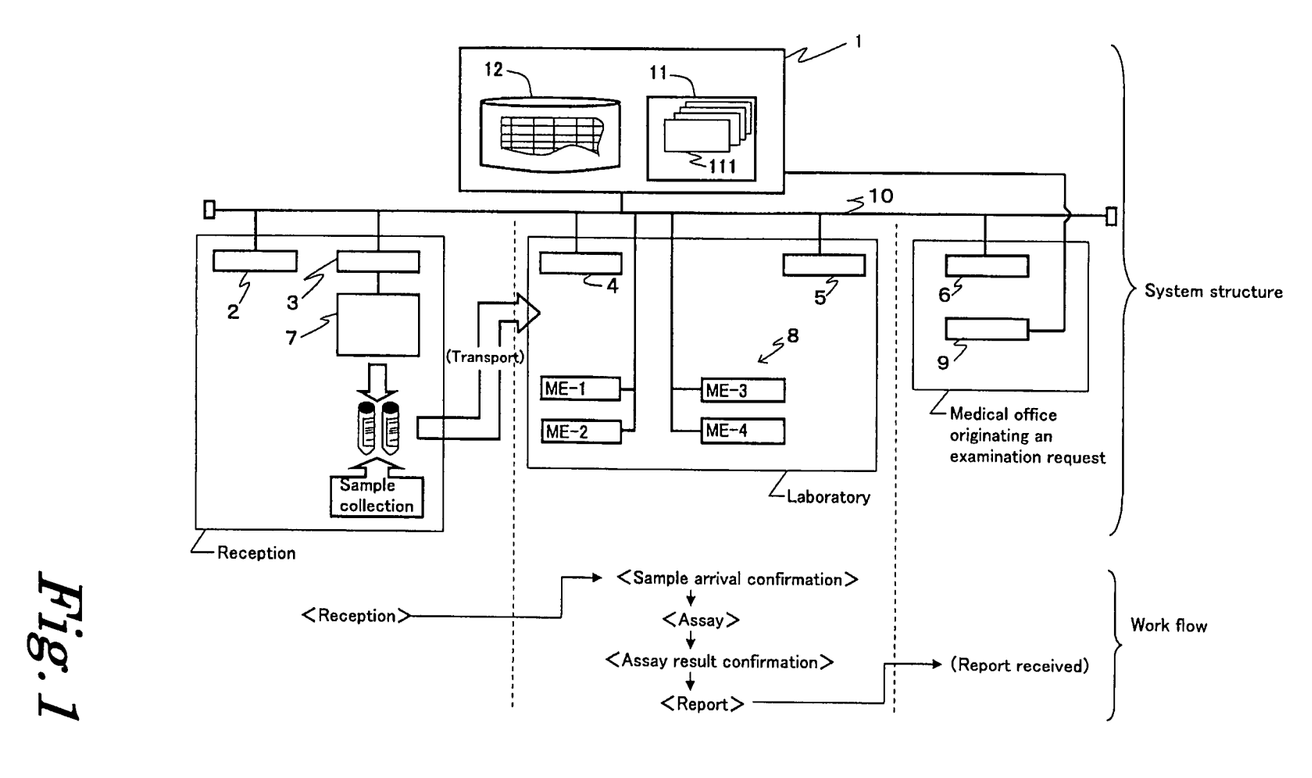
FIG. 1 illustrates the relationship between the structure of a clinical laboratory system and various clinical examination operations.

FIG. 1 illustrates the relationship between the structure of a clinical laboratory system and various clinical examination operations. This clinical laboratory system is a client/server type system including computers (server 1, and clients 2, 3, 4, 5, 6), sample container supply device 7, a group of analyzers 8 (ME-1, ME-2, ME-3, ME-4), and FAX 9, wherein each of the structural elements are connected by a local area network (LAN).

The computers (server 1, and clients 2, 3, 4, 5, 6) are general purpose computers having a CPU, ROM, RAM, hard disk and the like, and each is provided with input devices, such as a keyboard, mouse, and the like, and a display device, such as a CRT, LCD, and the like. Each client functions as an input/output terminal device for various types of input and output to the system, which send and receive information to and from the server 1. When some type of device is connected to the client, that client can transmit and receive information to and from the connected device.

The server 1 functions as an input/output terminal device in the manner of each of the clients, and the server 1 functions as a management device for the overall system by receiving information transmitted from each client and analyzer, and storing and managing a program group 11 for performing information processing, such as information storage and output, based on the received information. Each client realizes various types of functions as an input/output terminal device by reading the program group 11 managed by the server 1 as necessary.

Furthermore, the server 1 manages an examination information database 12. The examination information database 12 stores various information related to examinations (examination information), such as patient attribute information, and examination results and input time and the like for each examination, which is a management object of the clinical laboratory system. The information stored in the database 12 is input by the various clients and analyzers in the various steps of the clinical laboratory operation (i.e., receiving samples, sample arrival confirmation, assays, assay result confirmation, report preparation, report output, and the like, all of which are described below) performed by the clients and analyzers.

A characteristic of a clinical laboratory system embodying features of the present invention is having progress management functions for storing information related to examinations which are management objects, checking the progress of the clinical laboratory work from the stored examination information, and when progress is delayed or a specific sample must be re-examined such that the operator must be alerted about the examination situation, outputting such an alert to the display device of the client. The progress management functions include the two functions of an "examination information collection function" for inputting and storing examination information in the examination information database 12, and a "progress management screen output function" for searching the examination information database 12 based on predetermined extraction criteria and extracting examination information meeting these extraction criteria, and preparing and outputting a progress management screen from the extracted examination information. These progress management functions are realized by the progress management program 111, which includes the program group 11 managed by the server 1, and operates on the sever 1 and clients which form the clinical laboratory system.

1. Examination Information Collection Function

The examination information collection function is described as steps pertaining to the chain of clinical examination work managed by the clinical laboratory system. The chain of clinical examination work in this clinical laboratory system includes reception, confirmation of sample arrival, assay, confirmation of assay result, and reports, as shown in FIG. 1. When each operation ends, the examination information from the client and analyzer used in the operation is input and stored in the examination information database 12.

Reception

When a physician determines that a patient requires an examination, the request for the examination is made in the medical office. An order specifying the name of the patient and the examination items is received and recorded with the request. The chain of examination information work begins in this way. The received information is input by an operator on a specific reception input screen displayed on the display device of the client 2 using input devices such as a mouse, keyboard, and the like. The input content is stored in the examination information database 12 managed by the server 1 when it is received.

Figure 2:
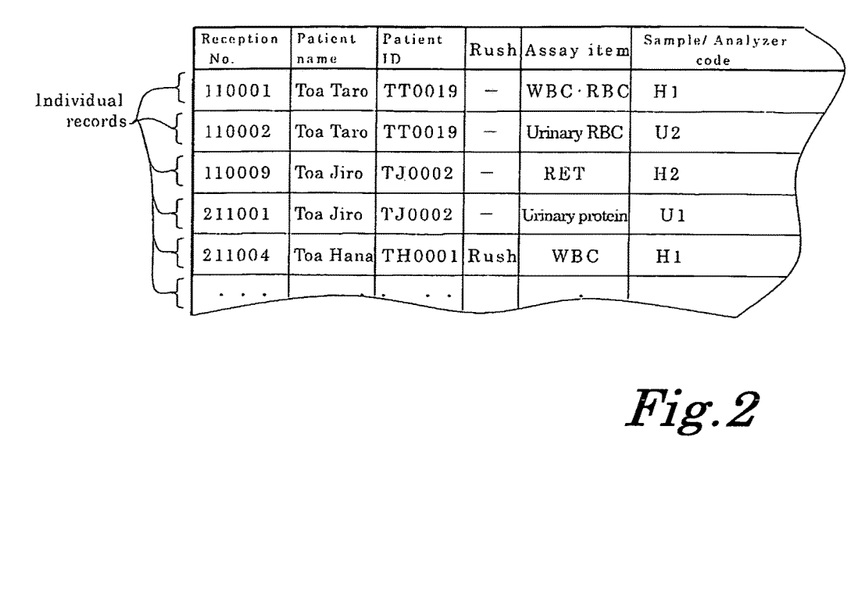
FIG. 2 shows an example of a data table of examination information input to an examination information database.

FIG. 2 shows an example of a data table of examination information input to the examination information database 12 from the client 2. The examination information database 12 has a record of each received examination, and stores information such as the "reception number" input at the time of reception, "patient name," "patient ID," "whether or not it is a rush examination," "examination items," and "sample and device specification codes" for specifying the analyzer and type of sample used. This information is stored the moment it is received. The information stored in the examination information database 12 and the records pertaining to the set of information contained therein are referred to as "examination information" throughout this description.

Since the type and number of sample containers used differ depending on the type of sample, type of assay, and the analyzer, the type and number of sample containers must be suitable for the content of the examination received. First, the examination information input and stored by the client 2 is transmitted to the sample container supply device 7 from the server 1 over the network. The sample container supply device 7 accommodates a plurality of types of sample containers for collecting samples, and selects and supplies the number and type of sample containers in accordance with the received examination information. Furthermore, the sample container supply device 7 has a built-in barcode printer, which prints a barcode label that includes various types of information, such as sample date, reception number, sample container ID, type of analyzer used, and the like, and automatically adheres the printed barcode label on the selected sample container. In this way, the sample container supply device 7 supplies sample containers in accordance with the content of the examination. A sample, such as blood or urine collected from a patient, is accommodated in the supplied sample container.

Confirmation of Sample Arrival

The sample container accommodating the sample is transported to a laboratory, such as a blood examination laboratory or a urine examination laboratory. In FIG. 1, a plurality of examination rooms are represented as a single laboratory. When the sample collected from the patient arrives at the laboratory, a sample arrival confirmation is input. The sample arrival confirmation input is accomplished by reading the barcode label adhered to the sample container using the barcode reader (not shown) of the client 4 installed in the laboratory. When the barcode is unreadable by the barcode reader due to soiling or the like of the barcode, it is possible to input the confirmation on a predetermined sample arrival confirmation input screen displayed on the display device of the client 4 using an input device, such as a mouse, keyboard, and the like. When the sample arrival confirmation is input, the information and the time the sample arrival confirmation was input are stored in the examination information database 12 managed by the server 1.

Assays

The sample for which arrival has been confirmed is set in the analyzer and the requested examination items are assayed. Among the analyzers ME-1, ME-2, ME-3, and ME-4 included in the analyzer group 8, both ME-1 and ME-2 are blood analyzers. ME-1 is a blood analyzer for assaying the number of erythrocytes, leukocytes, and platelets, and the hemoglobin concentration in the blood. ME-2 is a blood analyzer for assaying reticulocytes. ME-3 and ME-4 are urine analyzers. ME-3 is a urine analyzer for assaying tangible components in the urine, such as erythrocytes, leukocytes, bacteria, and casts, and is used for so-called urine sediment analysis. ME-4 is a urine analyzer for assaying optical components in the urine, such as protein, glucose, and occult blood, and is used for so-called urine qualitative analysis. Any of the analyzers included in the analyzer group 8 can read the barcode adhered to the sample container so as to completely automate the assay of the requested examination item.

The analyzers ME-1, ME-2, ME-3, and ME-4 are connected, respectively, to the network and the server 1, and when the assay ends in each analyzer, the assay result and information of the reception number, sample container ID, and assay date are automatically transmitted and input in the server 1. The assay result and the time the assay result was input are stored in the examination information database 12 managed by the server 1. Each analyzer can be said to function as a terminal device in this clinical laboratory system similar to other clients. When examinations are conducted manually without using these analyzers, it is possible to input the assay result in the assay result input screen displayed on the display device of the client 4 using input devices, such as a mouse, keyboard, and the like. In this case, the assay result and the time the assay result was input are stored in the examination information database 12.

Assay Result Confirmation

The assay result confirmation includes the operations of validation and re-examination instructions. Validation acknowledges that a specific assay result "may be reported to the requestor as an official assay result," and this operation can only be performed by an authorized operator. The validation is input to a predetermined validation input screen displayed on the display device of the client 5 using an input device, such as a mouse, keyboard, and the like. The assay result of the validation object is displayed on this screen, and the validation is input by selecting the "validation accepted" selection on the screen. When the validation is input, the validation input and the input time are stored in the examination information database 12 managed by the server 1.

Abnormal assay results are discovered during the validation operation. Sample abnormalities and analyzer abnormalities may be considered as causes for an abnormal assay result. When it is determined that re-examination is required, the operator outputs instructions for re-examination without validating the assay result. This is the re-examination instruction. When the re-examination instruction is output, the assay result determined to require re-examination is selected on the validation input screen, and the re-examination instruction is executed. The examination instruction and the input time for the sample for which the re-examination instruction has been output are stored in the examination information database 12.

Validation is not performed for the assay result for which the re-examination instruction has been output, and the sample is subjected to re-examination. When re-examination ends, the assay result of the re-examination and the time of the assay result of the re-examination are stored in the examination information database 12.

Regarding the re-examination, the initial assay result and the re-examination assay result are displayed on the validation input screen so that the operator can compare both results. When the re-examination assay result can be reported as an official assay result, the re-examination assay result is validated and input.

Reports

When the validation of the assay result ends, an assay report is prepared and transmitted from the laboratory to the medical office that originally requested the examination. Report preparation is accomplished by the operator inputting the necessary items on a predetermined report preparation screen displayed on the display device of the client 5 using an input device, such as a mouse, keyboard, and the like. When the report preparation ends, the data of the prepared report are transmitted to the server 1, and stored in the server 1 associated with the examination information records stored in the examination information database 12. These data are transmitted from the server 1 to the FAX 9 via a FAX modem (not shown). The FAX 9 is disposed in the medical office originally requesting the examination, and prints the data of the received report. When the information transmission from the server 1 to the FAX 9 ends, the time the transmission ends is stored in the examination information database 12. The data of the report stored on the server 1 can be viewed on a predetermined report access screen displayed on the display device of the client 6 disposed in the medical office originally requesting the examination.

Figure 3:
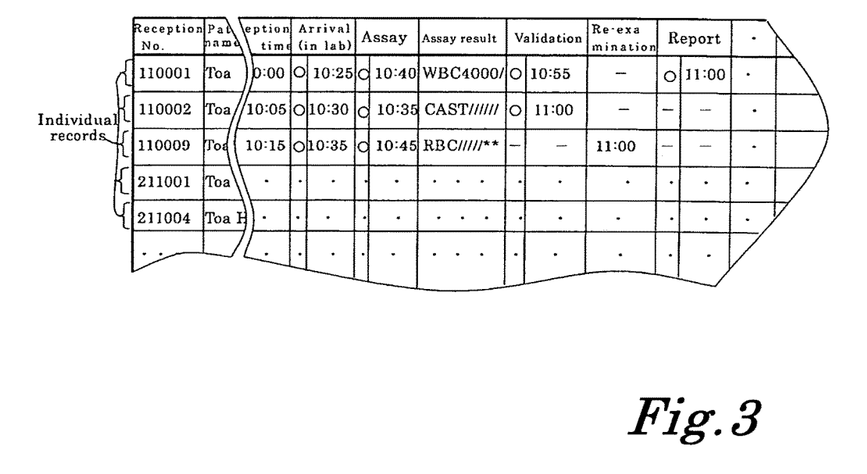
FIG. 3 shows an example of a data table of examination information input to an examination information database.

In this way, various types of information can be input and stored as examination information in the examination information database 12 from the clients and analyzers used for various operations at the time such operations have been completed. FIG. 3 shows an example of a data table of examination information input to the examination information database 12 from clients and analyzers. The reception number, patient name, patient ID, examination type, sample type/analyzer ID code, and the like are stored in each record. Furthermore, as has been previously mentioned, the time each operation of the clinical examination has been completed is also recorded and stored. The operations for which the time of the operations have been recorded in the examination information database 12 are previously completed operations. If the time is not recorded, the operation has not been completed. For example, in the examination record having reception number 110002, reception, arrival confirmation, assay, and validation have been completed, but the report has not yet been completed. Furthermore, when the time is recorded in the "re-examination" column, it indicates that a re-examination instruction has been output for this examination.

The examination information collection function is normally executed while the clinical laboratory system is operating, and input of examination information from the clients and analyzers can be received at any time and stored in the examination information database 12.

Figure 4:
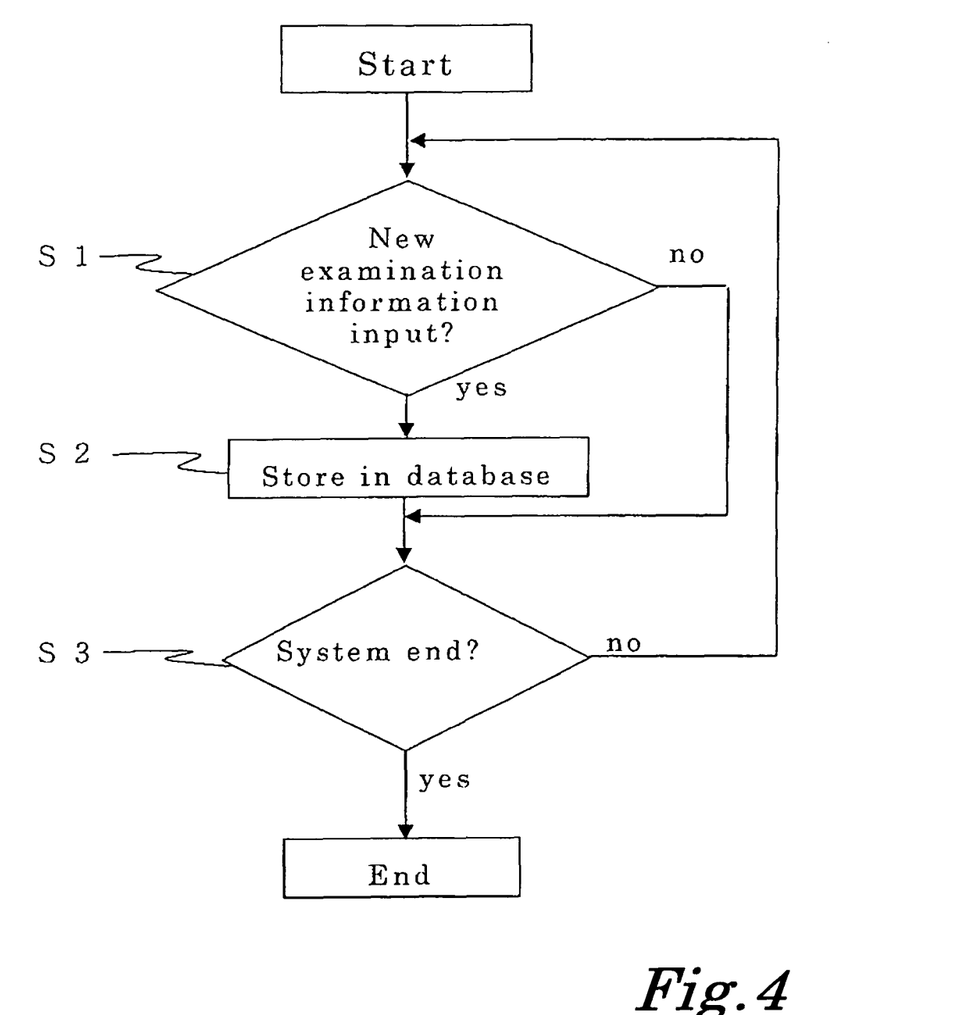
FIG. 4 illustrates the operation of a progress management program.

Information Processing Flow During Examination Information Collection Function Execution The input and recording of the examination information performed in the examination information collection function described above (i.e., at each step in the chain of the clinical examination operations) in the examination information database 12 is realized by the progress management program 111 executed on the computers forming the clinical laboratory system. FIG. 4 shows the operation flow of the progress management program 111 during the execution of the examination information collection function. The execution of the examination information collection function starts when the clinical laboratory system starts operation and, normally, is executed during the operation of the clinical laboratory system.

S1: During the operation of the clinical laboratory system, input examination information from clients and analyzers can be received and stored at any time. When examination information is input, the routine moves to S2, whereas when there is no information input, the routine moves to S3.

S2: Input examination information is stored in the examination information database 12.

S3: When the clinical laboratory system operates continuously, the routine moves to S1 and examination information input is continuously received. When the operation of the clinical laboratory system ends, the execution of the examination information collection function also ends.

The examination information collection function is executed by the progress management program 111 described above, and each client and analyzer can input examination information to the examination information database 12.

2. Progress Management Screen Output function

As previously described, the progress management function, which is realized in this clinical laboratory system by means of the progress management program 111, includes the progress management screen output function described below in addition to the examination information collection function described in section 1.

In the chain of laboratory operations from the reception of an examination to the report of the examination, there may be times when an operator is required to take countermeasures for delayed progress due to problems, or when re-examination is necessary. The progress management screen output function of this clinical laboratory system is defined as conditions which meet predetermined extraction criteria, such that when examination information meeting the extraction criteria is present in the examination information database 12, a predetermined screen is output to the display device of the client to alert the operator.

When the progress management screen output function is executed by the progress management program 111 on any client, only examination meeting the predefined extraction criteria are extracted from the examination information database 12, and summarily displayed as a predetermined progress management screen. The operator views the progress management screen and is directly alerted when an issue arises requiring a response relating to the displayed examination.

The progress management screen output function may be executed on any of the clients 2, 3, 4, 5 or 6. When the progress management screen output is executed by any client, the information processes in the "range selection," "extraction," and "output" described below are performed by the progress management program 111.

Range Selection

Figure 5:
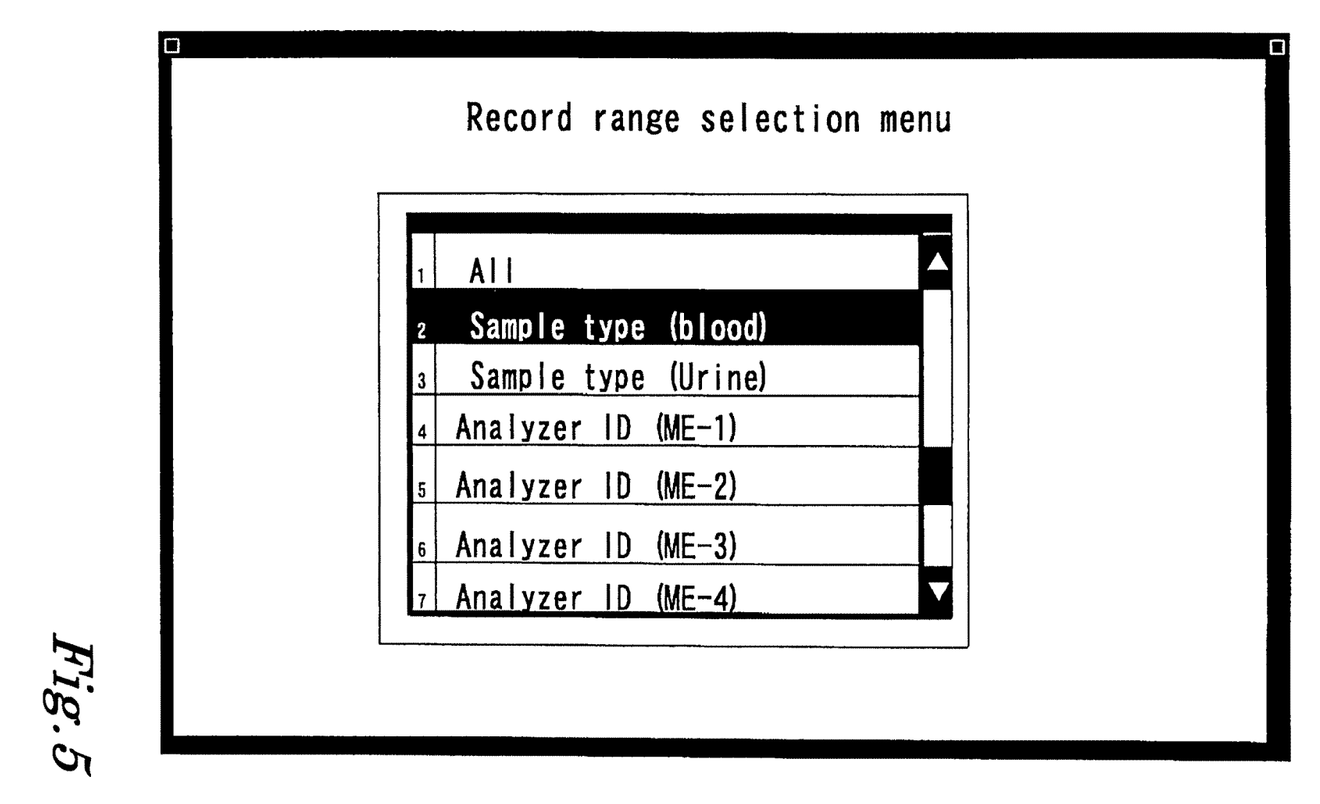
FIG. 5 shows an example of a screen used by an operator for selecting a range of examination information.

In the range selection step, a range of examination information is selected as an object for the progress management screen output from among the examination information recorded in the examination information database 12. When the execution of the progress management screen output function begins, a screen is displayed on the display device of the client which requests the operator to select an examination range via the progress management program 111. This screen is stored on the hard disk of the server 1. An example of this screen is shown in FIG. 5. In this screen, the range selection menu shows "All," "Sample type (blood)," "Sample type (urine)," "Analyzer (ME-1)," "Analyzer (ME-2)," "Analyzer (ME-3)," "Analyzer (ME-4)." Any range of examination information shown on the screen can be selected as an object for progress management-screen output by using an input device, such as a mouse, keyboard, and the like. In FIG. 5, "Sample type (blood)" is selected on the selection menu and displayed in reverse color. When "All" is selected, then in the "extraction" step described below, all examination records stored in the examination information database 12 are targeted and retrieved via the predetermined extraction criteria. When the "Sample type (blood)" is selected, then in the "extraction" step described below, only examination records for blood examinations are targeted and retrieved via the predetermined extraction criteria from among the examination information recorded in the examination information database 12. When "Sample type (urine)" is selected, then in the "extraction" step described below, only examination records for urine examinations are targeted and retrieved via the predetermined extraction criteria from among the examination information recorded in the examination information database 12. When "Analyzer (ME-1)" is selected, then in the "extraction" step described below, only records of examinations performed using the analyzer ME-1 are targeted and retrieved via the predetermined extraction criteria from among the examination information recorded in the examination information database 12. When "Analyzer (ME-2)" is selected, then in the "extraction" step described below, only records of examinations performed using the analyzer ME-2 are targeted and retrieved via the predetermined extraction criteria from among the examination information recorded in the examination information database 12. When "Analyzer (ME-3)" is selected, then in the "extraction" step described below, only records of examinations performed using the analyzer ME-3 are targeted and retrieved via the predetermined extraction criteria from among the examination information recorded in the examination information database 12. When "Analyzer (ME-4)" is selected, then in the "extraction" step described below, only records of examinations performed using the analyzer ME-4 are targeted and retrieved via the predetermined extraction criteria from among the examination information recorded in the examination information database 12.

In this clinical laboratory system, when the operator requires progress management only for blood examinations without requiring progress management for urine examinations, then in the "Range selection" step, the single selection "Sample type (blood)" may be selected from the range selection menu to limit the range of examination information by the type of sample used in the examination. In this way, it is possible to target only those samples subjected to blood examinations for which problems arise affecting progress, and display these problem examinations on the progress management screen. An operator who desires to target for progress management those examinations related to reticulocyte assay may select only the "Analyzer (ME-2)" from the selection menu so as to limit the range of examination information by the analyzer used for the examination. Thus, it is possible to target only those samples subjected to reticulocyte examinations performed by the analyzer ME-2, which has the function of reticulocyte assay, for which problems arise affecting progress, and display these problem examinations on the progress management screen. Furthermore, an operator who requires progress management for all examinations managed by the clinical laboratory system may select "All." In this way, examination information relating to examinations for which problems arise affecting progress may be extracted from among all examination information recorded in the examination information database 12, and these problems can be displayed on the progress management screen.

The "range selection" step described above is realized by the operation of the progress management program 111.

Extraction

Figure 6:
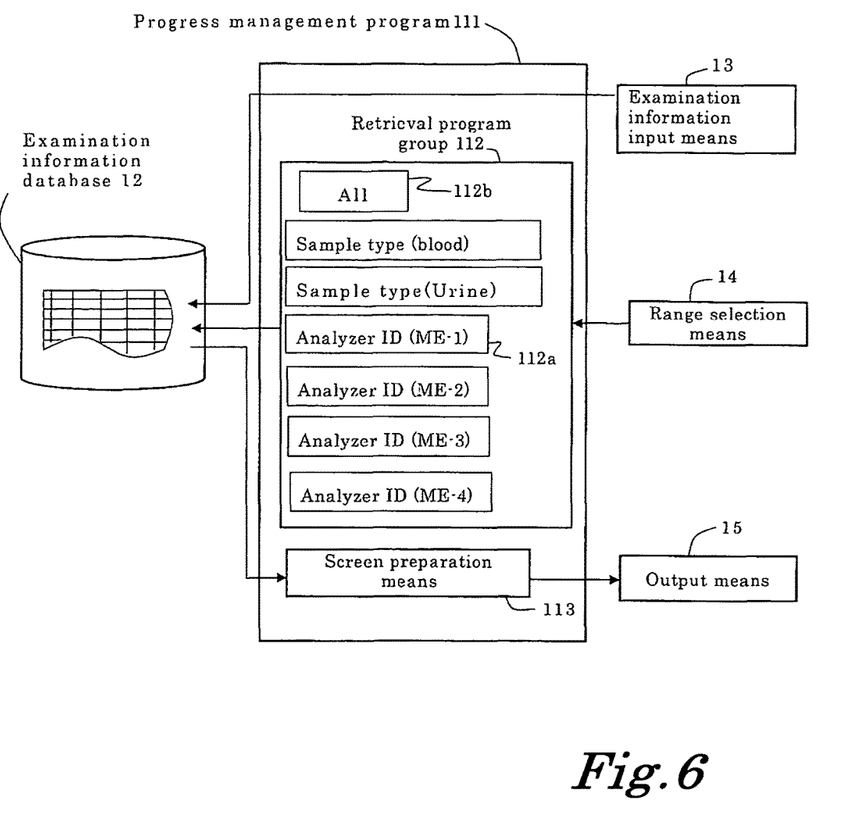
FIG. 6 describes the functions of a clinical laboratory system.

When "Range selection" is performed, examination information meeting the predetermined extraction criteria is retrieved and extracted from among examination information stored in the examination information database 12 in accordance with the selected range of examination information. FIG. 6 is a schematic drawing of the functions of the clinical laboratory system centered around the progress management program 111. Examination information input from the examination information input means 13 (in this instance, the input devices of each client or analyzer) by executing the examination information collection function via the progress management program 111 is stored in the examination information database 12. The progress management program 111 includes a retrieval program group 112 for retrieval using the predetermined extraction criteria in accordance with each range of examination information selected using the range selection means 14 (in this case, the input devices of each client). Each retrieval program is associated with a selection of the selection menu of the range selection displayed on the screen in FIG. 5, and retrieval is performed by starting a retrieval program corresponding to the input range selection. The predetermined extraction criteria used for retrieval are created in macro language for each retrieval program, and can be set such that the extraction criteria used for retrieval differs depending on the selected range of examination information.

Figure 7A:
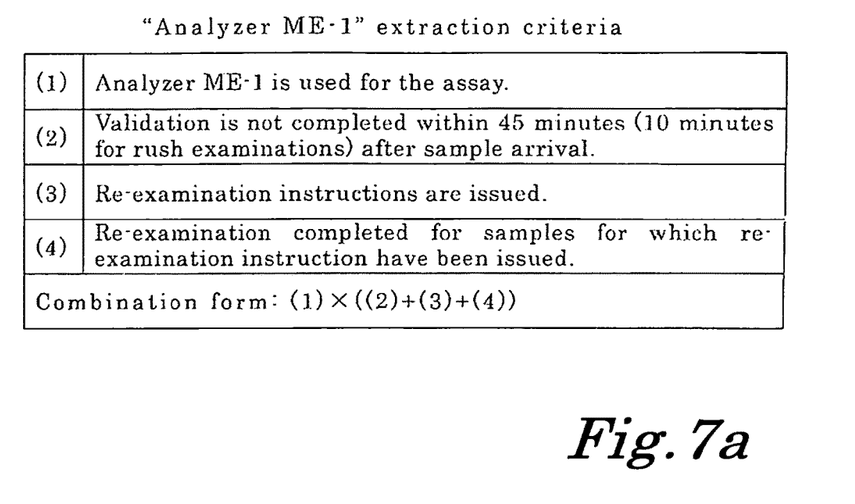
FIG. 7 shows the content of extraction criteria written in macro language in a retrieval program.

For example, when "Analyzer ME-1" is selected in "Range selection," the corresponding retrieval program 112a starts. FIG. 7a shows the content of the extraction criteria written in macro language in the retrieval program 112a corresponding to the "Analyzer ME-1" selection menu in the range selection. The criteria in this instance are set as described below.

(1) Examinations performed using the analyzer ME-1.
(2) Validation is not completed even though 45 minutes have elapsed since the sample arrived (10 minutes in the case of rush examinations).
(3) Re-examination instructions are issued.
(4) Re-examination is completed for samples having re-examination instructions.

The criteria (1) through (4) above are set in the combination form "(1)×((2)+(3)+(4))" (where "×" represents an AND condition, and "+" represents an OR condition). Retrieval is performed using this combination form as extraction criteria. That is, when this retrieval program 112a is executed, examination information meeting criterion (1) ("examinations performed using analyzer ME-1") and meeting any of the criteria (2), (3) or (4) are retrieved and extracted from among the records stored in the examination information database 12.

Regarding criterion (1), the retrieval program 112a retrieves records of examinations performed using the analyzer ME-1 based on the sample type/analyzer ID code recorded in each recorded in the examination information database 12.

With respect to criteria specifying whether or not a fixed time has elapsed since a standard time, as in criterion (2), the retrieval program 112a calculates the time difference from a standard time (in criterion (2), the sample arrival time) to the present, and compares the calculated time difference with a fixed time set in the criteria (in criterion (2), 45 minutes for normal examinations and 10 minutes for rush examinations). In this way, the examination is determined to meet or not meet the criteria.

Regarding criteria (3) and (4), which are not related to elapsed time, determinations are made by the presence or absence of input of each item of the examination information. In the case of determination by criterion (3), if a re-examination instruction is input, the examination information is determined to meet the criterion. If there is no input, the examination information is determined to not meet the criterion. In the case of determination under criterion (4), if re-examination completion has been input, the examination information is determined to meet the criterion. If there is no input, the examination information is deemed to not meet the criterion.

Figure 7B:
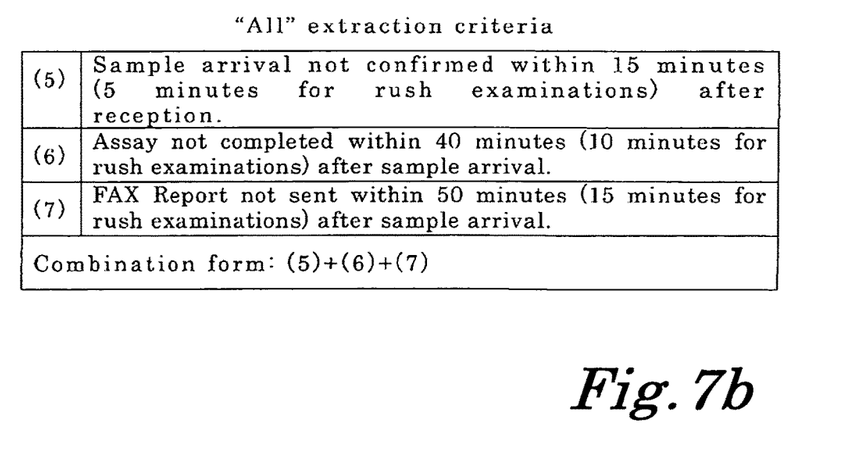

The combination form using these individual criteria are described as extraction criteria similar to the retrieval programs corresponding to the selection menu of the other range selections. FIG. 7b shows the content of the extraction criteria written in macro language in the retrieval program 112b corresponding to "All." These criteria are set as described below.

(5) No confirmation that the sample has arrived although 15 minutes has elapsed since reception (5 minutes for rush examinations).

(6) Assay is not completed even though 40 minutes has elapsed since sample arrival (10 minutes for rush examinations).

(7) The report Fax transmission is not completed even though 50 minutes has elapsed since the sample arrival (15 minutes for rush examinations).

The above-mentioned criteria (5), (6), and (7) are set in the combination form of "(5)+(6)+(7)" (where "+" represents an OR condition). That is, when the retrieval program 112b is executed, samples meeting the condition of any of the criteria (5), (6) or (7) are retrieved and extracted from among the samples recorded in the examination information database 12.

The predetermined time for which the criteria (2), (5), (6), and (7) are set may be applied to normal examinations or rush examinations. Any of the criteria used in the present embodiment may be set so that the time for rush examinations is shorter compared to the time for normal examinations. In this way, progress delays can be checked at an earlier stage for rush examinations compared to normal examinations so that the operator can be alerted.

The above-mentioned extraction steps are executed when the client reads each retrieval program included in the retrieval program group 112.

Output

The progress management program 111 prepares the data for the progress management screen based on the content of the examination information included in the extracted records. The prepared data are output to the display device of a client as a progress management screen. The output steps described above are executed when the client reads the progress management program 111.

Figure 8:
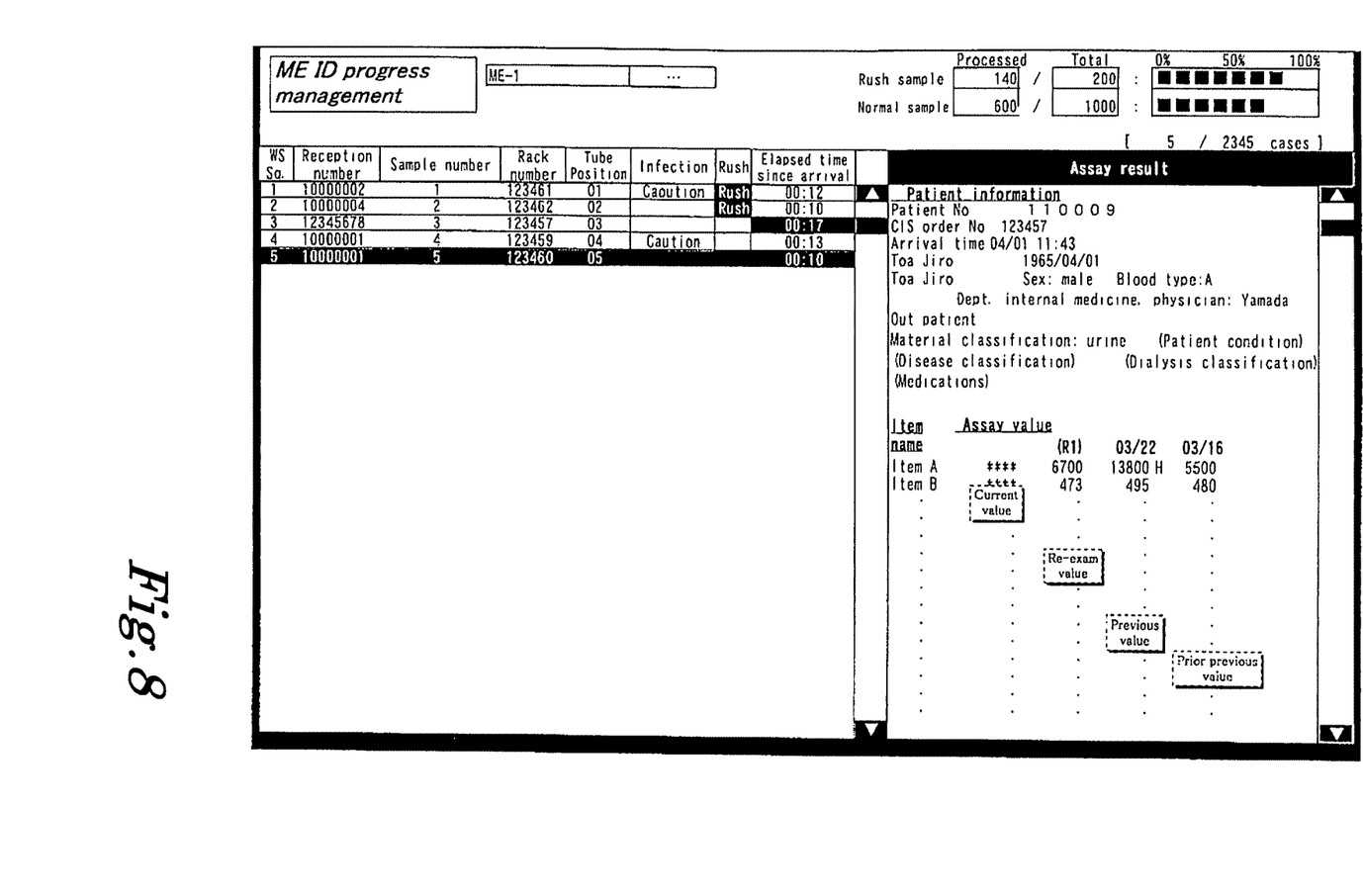
FIG. 8 shows an example of a progress management screen.

FIG. 8 shows an example of the progress management screen output to the display device of a client when the "Analyzer ME-1" has been selected in "Range selection." In this case, the examinations which have been determined to meet the extraction criteria are displayed on the left side of the screen. Displayed with each examination is the sample reception number, sample number and, whether or not it is a rush examination (in the case of a rush examination, "Rush" is displayed in the "Rush" column). Furthermore, whether or not a fixed time has elapsed since the arrival of the sample was confirmed is displayed in the "Elapsed time since arrival" column. The displayed examinations meet criterion (2) (validation incomplete even though 45 minutes, 10 minutes for rush examinations, have elapsed since sample arrival), and the elapsed time is displayed after 45 minutes (10 minutes for rush examinations) has elapsed since the sample arrived. The time displayed in the "Elapsed time since arrival" column is used in calculations when comparing the examination report and criteria. This displayed list is sorted in the sequence of rush examinations, then normal examinations, and each category is sorted and displayed sequentially based on the elapsed time since arrival.

When any of the listed examinations are selected, various types of information relating to the selected examinations (patient name, patient number, birth date, patient attributes such as blood type, past assay results for this patient, current assay results for this patient, and the like) are displayed on the right side of the screen. The selected examination is displayed in the list with the text and background colors reversed.

Examinations which do not meet the criteria are not displayed on the progress management screen. That is, since the operator only selects and displays examinations requiring some type of countermeasure, there is no concern that the operator might overlook an examination requiring a countermeasure from among those in the displayed list (only the required examinations are displayed).

On the upper right side of the screen are displayed the total number of samples currently received for examination, and the number of these samples that have been processed as rush and normal examinations. In this way, the progress of all examinations can be managed.

Figure 9:
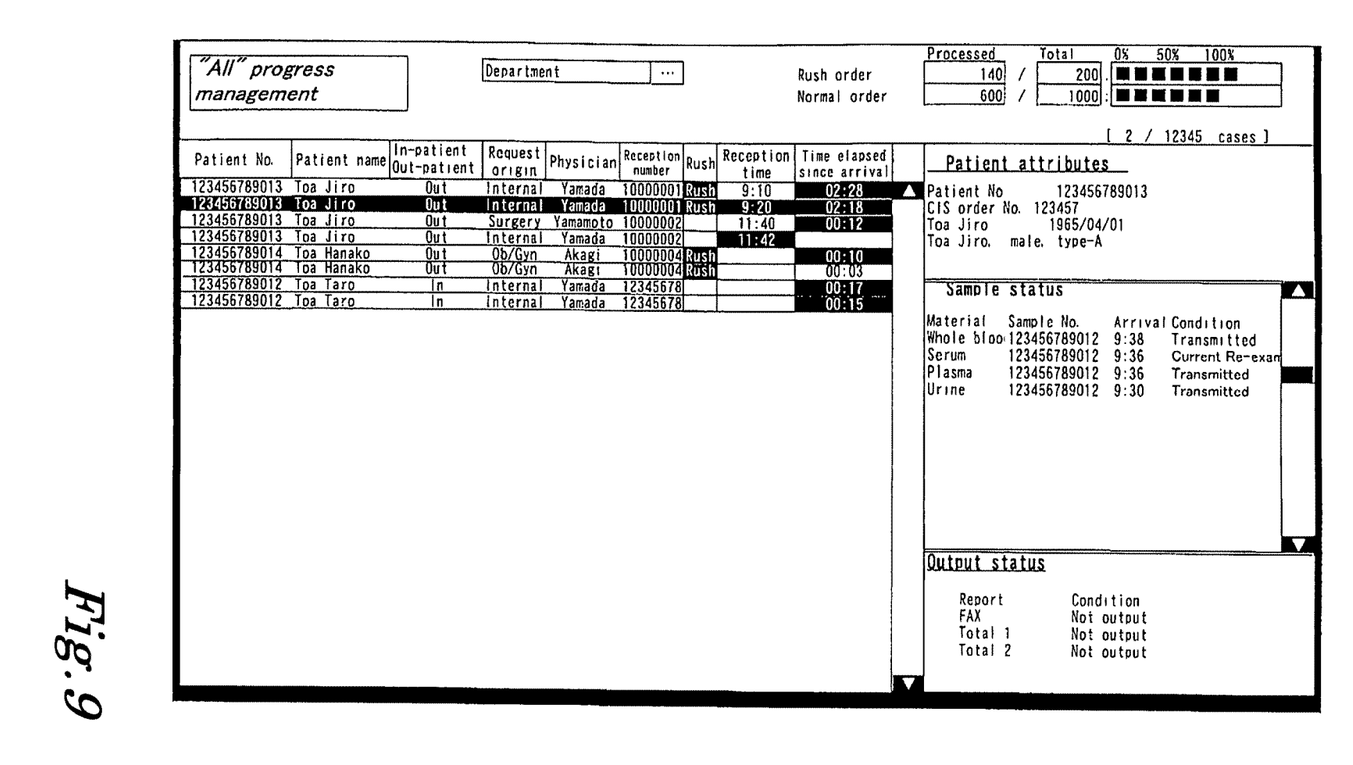
FIG. 9 shows an example of a progress management screen.

FIG. 9 shows an example of the progress management screen displayed on the display device of a client when "All" is selected in "Range selection." In this case, examinations which are determined to meet the extraction conditions are displayed on the left side of the screen. Displayed with each examination are the patient number, patient name, whether or not the patient is an outpatient or an in-patient, name of the medical office issuing the original request for examination, reception number, whether or not it is a rush examination (in the case of a rush examination, "Rush" is displayed in the "Rush" column), and the time the same was received. Furthermore, whether or not a fixed time has elapsed since the sample arrival was confirmed is displayed in the "Elapsed time since arrival" column.

In the list display, examinations for which the reception time is displayed but elapsed time since arrival is not displayed, are examinations that meet criterion (5) (examination arrival has not been confirmed 15 minutes after arrival, 5 minutes for rush examinations). Examinations for which the elapsed time since arrival is displayed are examinations that meet criterion (6) (assay has not been completed 40 minutes since sample arrival, 10 minutes for rush examinations), or criterion (7) (report FAX transmission has not been completed 50 minutes after sample arrival, 15 minutes for rush examinations). Whether or not an examination meets either criterion (6) or (7) can be known by confirming the condition of the current sample by referring to the "Sample status" column displayed on the right side of the list display.

When any examination in the list display is selected using an input device such as a mouse or keyboard, details of this examination are shown in the Sample status column. When any examination which is not in the list display is selected, patient attribute information relating to the selected examination is shown in the "Patient attributes" column, and whether or not a report has been output by FAX is shown in the "Output status" column. The selected examination is displayed in the list display with the text and background in reverse colors.

The total number of examination orders currently received, and the number of corresponding processed orders are displayed with the rush and normal examinations differentiated. In this way, the progress of all examinations can be managed.

Figure 10:
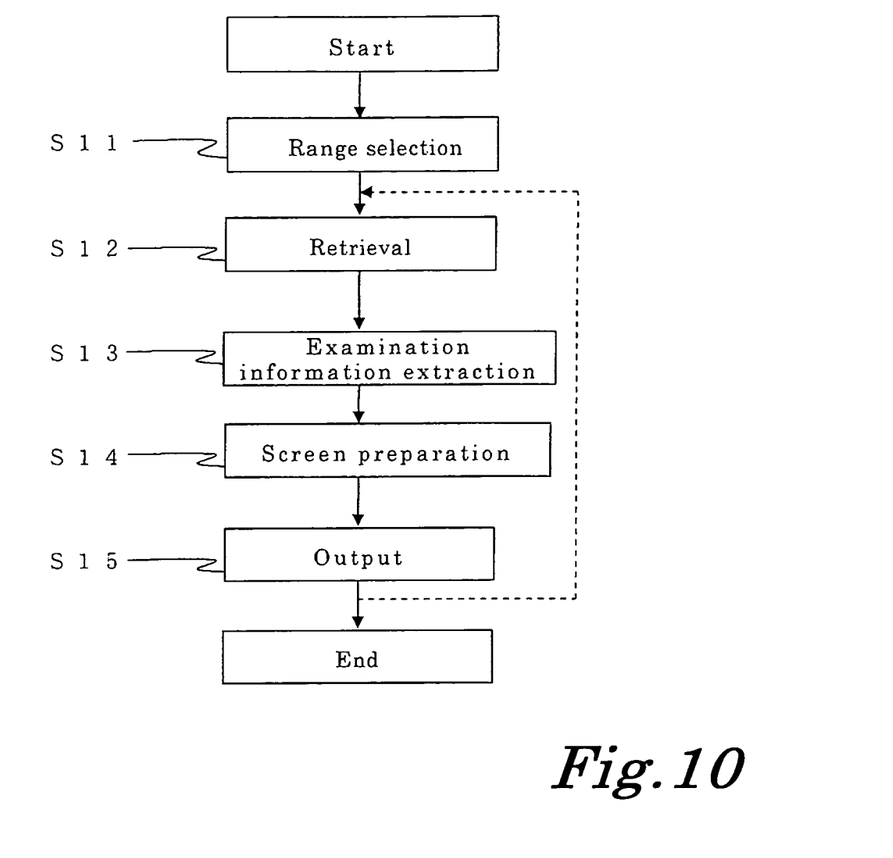
FIG. 10 illustrates the operation of a progress management program.

Information Processing Flow During Execution of the Progress Management Screen Output Function FIG. 10 shows the operation flow of the progress management program 111 when the progress management screen output function is executed. When any client begins executing the progress management screen output function, the following are executed.

S11: Range selection input is received. Then, the routine moves to S12.

S12: The retrieval program corresponding to the range of the selected examination information is started based on the range selection input, and information is retrieved form the examination information database 12. Then, the routine moves to S13.

S13: The records meeting the extraction criteria are extracted from the examination information database 12. Then, the routine moves to S14.

S14: Data are prepared for output as the progress management screen based on the examination information of the extracted records. Then, the routine moves to S15.

S15: The progress management screen is displayed by outputting the prepared data to the display device of the client.

When the progress management screen display does not end and the display continues in the currently selected range of examination information, the routine returns from S15 to S12 (represented by the dashed arrow in FIG. 10), and the processes from S12 through S15 are repeated. By periodically repeating this cycle, the progress management screen is updated and the input content displayed even when new data have been input in the examination information database 12. Therefore, when a situation arises which requires that the operator respond promptly, the operator can rapidly execute countermeasures because the screen updating is repeated periodically.

Although screen updating is performed periodically with a predetermined screen update timing in the above embodiment, such screen updating may be reliably performed every time there are new data input to the examination information database 12. For example, when new examination information is input while the progress management screen is being displayed, the progress management program 111 may retrieve and extract the new information via the retrieval program corresponding to the range of examination information selected at that time, and prepare display data so as to update the output content of the progress management screen. In this way, the operator is able to take prompt countermeasures because the progress management screen is updated in real time even when situations arise which require rapid action by the operator.

Furthermore, when new examination information is input, the progress management program 111 performs retrieval by a retrieval program having predetermined extraction criteria, and if examination information meeting the predetermined extraction criteria is present, the operator may be alerted. This alert may be accomplished when the progress management screen is not displayed on the display device of the client when the operator is performing an operation other than progress management using the client. This alert may be an alert displayed on the display device of the client the operator is operating. Furthermore, this alert may be an audible alert.

Although the range of examination information can be optionally selected by the operator when executing the progress management screen output function in the aforesaid embodiment, the selection menu for the selectable range may be restricted in accordance with the authority of the operator. For example, operator log-in names may be stored beforehand on the server 1 for when an operator logs in to the clinical laboratory system. The log-in names and selectable range corresponding to these log-in names may be set in the progress management program. Then, when an operator inputs a range selection, the progress management program refers to the log-in names stored on the server 1, and restricts the selection menu of the selectable ranges in accordance with the log-in name. In this way, the managers responsible for the laboratory are able to optionally select any of the ranges "All," "Sample type," and "Analyzer type," whereas examination technicians who have authority only to operate analyzers associated with blood examinations (analyzers ME-1 and ME-2) but do not have authority to operate analyzers associated with urine examinations (analyzers ME-3 and ME-4), are only allowed to specify the ranges of "Sample type (blood)," "Analyzer (ME-1)" and "Analyzer ME-2)." According to this structure, a suitable progress management screen corresponding to the scope of operations performed by each operator can be rapidly displayed.

According to clinical laboratory systems embodying features of the present invention, an operator will not overlook an examination since only examinations requiring some type of countermeasure by the operator are extracted and displayed. Furthermore, since the ranges of "All," "Sample type," and "Analyzer type" can be specified, and only those examinations requiring countermeasures by the operator are selected and displayed, it is possible for the operator to display information for only those examinations that are not progressing properly within the management scope of the operator. In this way, when there are problems with progress, only the information truly required by the individual operator is displayed because examinations outside the management scope of the operator are not output to the progress management screen.

Furthermore, output updates are performed automatically and with a predetermined timing, such that the operator can rapidly respond to a situation requiring a prompt response, and the lead time in the chain of laboratory operations can be reduced.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A clinical laboratory system comprising a server computer and at least one client computer, the server computer being configured to:

create, in a database, an entry which comprises an identification of a patient, a type of analysis requested on a sample of the patient and an identification of analyzer capable of performing the requested type of analysis; and each time a workflow for analyzing the sample advances to a respective workflow point of a plurality of workflow points, which comprise at least some of (i) a point at which the sample is received, (ii) a point at which the sample is arrived, (iii) a point at which the requested type of analysis is completed on the sample, (iv) a point at which a result of the analysis is verified, and (v) a point at which a report is sent regarding the result of the analysis, update the entry by adding to the entry a time stamp indicating a chronology of progress to the respective workflow point, and the at least one client computer being configured to:

provide a progress management user interface on a display of the client computer, the progress management user interface comprising a selection screen that presents a plurality of screening options including options for (a) selecting all entries in the database, (b) selecting an entry in which a particular type of sample is analyzed and (c) selecting an entry in which a particular analyzer is used; and receive a selected one of the plurality of screening options via the progress management user interface and transmit the selected one of the screening options to the server computer, and the server computer being further configured to:

receive the selected one of the plurality of screening options from the at least one client computer;

extract entries from the database which meet the selected one of the plurality of screening options and which meet at least one of a plurality of time conditions, each of the plurality of time conditions comprising exceeding a predetermined time expected for an entry to take to advance to said one of the workflow points; and transmit the extracted entries to the at least one client apparatus, and the at least one client computer being further configured to:

receive the transmitted entries from the server computer; and provide the progress management user interface further comprising a progress management screen including a list of the received entries with times each entry has elapsed from a respective time of the time stamp that was added at one workflow point preceding said one of the workflow points.

2. The system according to claim 1, wherein the plurality of workflow points further comprise (vi) a point at which a re-examination is ordered and (vii) a point at which a re-examination is completed.

3. The system according to claim 1, wherein the server computer is configured to extract, from among the selected entries, an entry which meets both of a non-time condition for extracting an entry in which a re-examination is ordered and one of the plurality of time conditions.

4. The system according to claim 1, wherein the server computer is configured to extract, from among the selected entries, an entry which meets any one of the plurality of time conditions.

5. The system according to claim 1, wherein the elapsed time is measured from the respective time of the time stamp that was added at said one workflow point preceding said one of the workflow points.

6. The system according to claim 5, wherein said one workflow point preceding said one of the workflow points is one of (i) the point at which the sample is received, and (ii) the point at which the sample is arrived.

7. The system according to claim 1, wherein the elapsed time is expressed by an excess time over a predetermined time expected to take to advance to said one of the workflow points from said one workflow preceding said one of the workflow points.

8. The system according to claim 1, wherein the entry further comprises an indication of urgency of analyzing the sample.

9. The system according to claim 8, wherein the predetermined time varies according to the identification of urgency recorded in the entry.

10. The system according to claim 1, wherein the server computer is configured to restrict selection of a screening option which is unauthorized to access.

11. A server apparatus of a clinical laboratory system that comprises a database and at least one client apparatus, wherein the database is recorded with entries which each comprise an identification of a patient, a type of analysis requested on a sample of the patient and an identification of analyzer capable of performing the requested type of analysis, the at least one client apparatus is configured to display a selection screen that presents a plurality of screening options including options for (a) selecting all entries in the database, (b) selecting an entry in which a particular type of sample is analyzed and (c) selecting an entry in which a particular analyzer is used, and transmit a selected one of the plurality of screening options to the server apparatus, and the server apparatus comprises a processor of a computer system and a memory that stores programs executable by the processor to:

each time a workflow for analyzing the sample advances to a respective workflow point of a plurality of workflow points, which comprise at least some of (i) a point at which the sample is received, (ii) a point at which the sample is arrived, (iii) a point at which the requested type of analysis is completed on the sample, (iv) a point at which a result of the analysis is verified, and (v) a point at which a report is sent regarding the result of the analysis, update the entry by adding to the entry a time stamp indicating a chronology of progress to the respective workflow point;

receive the selected one of the plurality of screening options from the at least one client apparatus;

extract entries from the database which meet the selected one of the plurality of screening options and which meet at least one of a plurality time conditions, each of the plurality of time conditions comprising exceeding a predetermined time expected for an entry to take to advance to said one of the workflow points; and transmit the extracted entries to the at least one client apparatus for providing a user interface including a profress management screen including a list of the extracted entries with times each elapsed from a respective time of the time stamp that was added at one workflow point preceding said one of the workflow points.

12. The server apparatus according to claim 11, wherein the plurality of workflow points further comprise (vi) a point at which a re-examination is ordered and (vii) a point at which a re-examination is completed.

13. The server apparatus according to claim 11, wherein the server computer is configured to extract, from among the selected entries, an entry which meets both of a non-time condition for extracting an entry in which a re-examination is ordered and one of the plurality of time conditions.

14. The server apparatus according to claim 11, wherein the server computer is configured to extract, from among the selected entries, an entry which meets any one of at least some of the plurality of time conditions.

15. The server apparatus according to claim 11, wherein the elapsed time is measured from the respective time of the time stamp added at said one workflow point preceding said one of the workflow points.

16. The server apparatus according to claim 15, wherein said one workflow point preceding said one of the workflow points is one of (i) the point at which the sample is received, and (ii) the point at which the sample is arrived.

17. The server apparatus according to claim 11, wherein the elapsed time is expressed by an excess time over a predetermined time expected to take to advance to said one of the workflow points from said one workflow point preceding said one of the workflow points.

18. The server apparatus according to claim 11, wherein the entry further comprises an indication of urgency of analyzing the sample.

19. The server apparatus according to claim 18, wherein the predetermined time varies according to the identification of urgency recorded in the entry.

20. The server apparatus according to claim 11, wherein the server computer is configured to restrict selection of a screen option which is unauthorized to access.

21. A client apparatus of a clinical laboratory system which executes a workflow for analyzing samples, the clinical laboratory system comprising a server apparatus with a database recorded with entries which each comprise an identification of a patient, a type of analysis requested on a sample of the patient and an identification of analyzer capable of performing the requested type of analysis, wherein each time a workflow for analyzing the sample advances to a respective workflow point of a plurality of workflow points, which comprise at least some of (i) a point at which the sample is received, (ii) a point at which the sample is arrived, (iii) a point at which the requested type of analysis is completed on the sample, (iv) a point at which a result of the analysis is verified, and (v) a point at which a report is sent regarding the result of the analysis, the server apparatus updates the entry by adding to the entry a time stamp indicating a chronology of progress to the respective point, the client apparatus comprising a processor of a computer system and a memory that stores programs executable by the processor to:

provide a progress management user interface on a display of the client computer, the progress management user interface comprising a selection screen that presents a plurality of screening options including options for (a) selecting all entries in the database, (b) selecting an entry in which a particular type of sample is analyzed and (c) selecting an entry in which a particular analyzer is used;

receive a selected one of the plurality of screening options via the profress management user interface and transmit the selected one of the plurality of screening options to the server apparatus;

receive entries from the server which meet the selected one of the plurality of screening options and at least one of a plurality of time conditions, each of the plurality of time conditions comprising exceeding a predetermined time expected for an entry to take to advance to said one of the workflow points; and provide the progress management user interface further comprising a progress management screen including a list of the received entries with times each entry has elapsed from a respective time of the time stamp that was added at one workflow point preceding said one of the workflow points.

22. The client apparatus according to claim 21, wherein the plurality of workflow points further comprise (vi) a point at which a re-examination is ordered and (vii) a point at which a re-examination is completed.

23. The client apparatus according to claim 21, wherein the client apparatus is configured to receive, from the server apparatus, an entry which meets both of a non-time condition for extracting an entry in which a re-examination is ordered and one of the plurality of time conditions.

24. The client apparatus according to claim 21, wherein the client apparatus is configured to receive, from the server apparatus, an entry which meets any one of at least some of the plurality of time conditions.

25. The client apparatus according to claim 21, wherein the elapsed time is measured from the respective time of the time stamp that was added at said one workflow point preceding said one of the workflow points.

26. The client apparatus according to claim 25, wherein said one workflow point preceding said one of the workflow points is one of (i) the point at which the sample is received, and (ii) the point at which the sample is arrived.

27. The client apparatus according to claim 21, wherein the elapsed time is expressed by an excess time over a predetermined time expected to take to advance to said one of the workflow points from said one workflow point preceding said one of the workflow points.

28. The client apparatus according to claim 21, wherein the entry further comprises an indication of urgency of analyzing the sample.

29. The client apparatus according to claim 28, wherein the predetermined time varies according to the identification of urgency recorded in the entry.

30. The client apparatus according to claim 21, wherein the client apparatus is configured to be restricted by the server apparatus from selecting a screen option which is unauthorized to access.

* * * * *